United States Patent
Emmerling

(10) Patent No.: US 10,485,687 B2
(45) Date of Patent: Nov. 26, 2019

(54) DEVICE FOR MANAGING PATELLOFEMORAL PAIN AND METHODS OF USE THEREOF

(71) Applicant: K-Neesio LLC, Rochester, NY (US)

(72) Inventor: Michael J. Emmerling, Macedon, NY (US)

(73) Assignee: K-Neesio LLC, Rochester, NY (US)

( * ) Notice: Subject to any disclaimer, the term of this patent is extended or adjusted under 35 U.S.C. 154(b) by 0 days.

(21) Appl. No.: 16/023,971

(22) Filed: Jun. 29, 2018

(65) Prior Publication Data
US 2019/0000660 A1 Jan. 3, 2019

Related U.S. Application Data

(60) Provisional application No. 62/564,444, filed on Sep. 28, 2017, provisional application No. 62/527,687, filed on Jun. 30, 2017.

(51) Int. Cl.
*A61F 5/00* (2006.01)
*A61F 5/01* (2006.01)

(52) U.S. Cl.
CPC .... *A61F 5/0109* (2013.01); *A61F 2005/0197* (2013.01)

(58) Field of Classification Search
CPC .... A61F 5/0109; A61F 5/0106; A61F 5/0104; A61F 5/01; A61F 5/0123; A61F 2005/0197; A61F 5/013; A61F 5/0118; A61F 5/0125; A61F 2005/0165; A61F 5/0102; A61F 2005/0167; A61F 2005/0179; A61F 5/04; A61F 5/042; A61F 5/048

See application file for complete search history.

(56) References Cited

U.S. PATENT DOCUMENTS 5,133,341 A 7/1992 Singer et al.
5,556,374 A * 9/1996 Grace .................. A61F 5/0109
602/20

(Continued)

FOREIGN PATENT DOCUMENTS

EP 3090708 A1 11/2016

OTHER PUBLICATIONS

McWalter, E.J., et al., "The Effect of a Patellar Brace on Three-Dimensional Patellar Kinematics in Patients with Lateral Patellofemoral Osteoarthritis," Osteoarthritis and Cartilage 19(7), pp. 801-808 (2011).

(Continued)

*Primary Examiner* — Victoria J Hicks
(74) *Attorney, Agent, or Firm* — Pepper Hamilton LLP

(57) ABSTRACT

A device for managing patellofemoral pain includes a wearable anchor structure configured to be positioned adjacent to the knee joint of a user. A spring mechanism is attachable, during use, to the anchor structure at first and second attachment positions located laterally and medially of the knee joint, respectively. An attachment component is coupled to the spring mechanism and has an attachment surface configured to be removably attached, during use, to the skin over the patella of the user such that the spring mechanism applies a tension force on the attachment component in an anterior direction. Methods for managing patellofemoral pain and realigning the patella and a patellofemoral pain management kit are also disclosed.

24 Claims, 11 Drawing Sheets

(56) References Cited

U.S. PATENT DOCUMENTS

| | | | |
|---|---|---|---|
| 6,287,269 | B1 | 9/2001 | Osti et al. |
| 8,435,197 | B2* | 5/2013 | Vollbrecht ............ A61F 5/0125 602/23 |
| 8,663,144 | B2 | 3/2014 | Farrow et al. |
| 8,926,539 | B2 | 1/2015 | Cropper |
| 9,021,614 | B2* | 5/2015 | Tepper ............... A41D 13/0153 2/22 |
| 9,393,147 | B2 | 7/2016 | Scheuermann et al. |
| 9,532,895 | B2 | 1/2017 | Romo |
| 2005/0020951 | A1 | 1/2005 | Gaylord et al. |
| 2008/0208095 | A1* | 8/2008 | Kazmierczak ........ A61F 5/0123 602/26 |
| 2009/0131844 | A1 | 5/2009 | Dean et al. |
| 2011/0137220 | A1 | 6/2011 | Vollbrecht et al. |
| 2012/0078151 | A1 | 3/2012 | Cropper |
| 2013/0110023 | A1 | 5/2013 | Scheuermann et al. |
| 2013/0245523 | A1 | 9/2013 | Romo |
| 2015/0290014 | A1 | 10/2015 | Anglada et al. |
| 2015/0313788 | A1 | 11/2015 | Conte et al. |
| 2016/0324675 | A1 | 11/2016 | Gomez et al. |
| 2017/0049600 | A1 | 2/2017 | Protasiewicz et al. |
| 2017/0065448 | A1* | 3/2017 | Michell ................. A61F 5/0102 |
| 2017/0143527 | A1 | 5/2017 | Nelson et al. |

OTHER PUBLICATIONS

Stein, B. E., et al., "Patellofemoral Disorders: An Overview", http://orthoinfo.aaos.org/topic.cfm?topic=A00590 (2016).

Foran, J. R. H., et al., https://www.hss.edu/conditions_patellofemoral-disorders-overview.asp (2018).

https://www.google.com/search?q=patellar+unloading+brace&oq=patella+unloa&aqs=chrome.4.69i57j69i59j0l4.23336j0j7&sourceid=chrome&ie=UTF-8, last accessed Jul. 13, 2018.

https://www.betterbraces.com/knee-injuries/patellofemoral-pain-runners-knee, last accessed Jul. 13, 2018.

International Search Report and Written Opinion for PCT/US 18/40386, dated Sep. 28, 2018.

* cited by examiner

DEVICE FOR MANAGING PATELLOFEMORAL PAIN AND METHODS OF USE THEREOF

This application claims the benefit of U.S. Provisional Patent Applications Serial No. 62/564,444 filed Sep. 28, 2017 and Ser. No. 62/527,687 filed Jun. 30, 2017, which are hereby incorporated by reference in their entirety.

FIELD OF THE INVENTION

The present invention relates to a device for managing patellofemoral pain, methods for managing patellofemoral pain and re-aligning the patella, and a patellofemoral pain management kit.

BACKGROUND OF THE INVENTION

Knee osteoarthritis (OA) is symptomatic in 12.1% of Americans over 60 years of age. The patellofemoral joint is involved in 50% of all radiographic knee osteoarthritis cases in either an isolated form or combined with tibiofemoral OA. Despite the prevalence of patellofemoral OA, the patellofemoral joint has received relatively little attention in the OA literature and there are few treatment options for individuals with patellofemoral OA.

The patella rests in a groove at the distal end of the femur called the trochlear groove. When the knee is extended and flexed, the patella tracks superiorly and inferiorly, respectively, inside the groove. Both the posterior aspect of the patella and the trochlear groove are covered with articular cartilage that allows the bones to glide smoothly along each other as the leg is flexed and extended.

Patellofemoral arthritis occurs when the articular cartilage lining the trochlear groove and on the posterior aspect of the patella deteriorates and becomes inflamed. The joint space in the knee is narrowed due to the patellofemoral arthritis. Additionally, bone spurs may develop due to the arthritis in the knee.

As the articular cartilage deteriorates it becomes frayed, and when the wear is severe, the underlying bone may become exposed. Moving the bones along this rough surface generates friction and can be painful. Overload osteoarthritis, a condition that resembles osteoarthritis in any other joint, i.e., a gradually progressive thinning of the cartilage related to "normal wear and tear" that in this case is restricted to, or starts in, the patellofemoral compartment of the knee, may also occur.

In additional to patellofemoral arthritis, patellofemoral pain may also be the result of patellofemoral pain syndrome, patellar tendonitis, chondromalacia, and patella maltracking.

There are numerous devices that have been developed and marketed to help alleviate patellofemoral pain. The currently available devices generally either attempt to adjust the patella position and movement by pushing it inward (posteriorly) and/or medially or laterally. Some devices attempt to reduce the load on the patella by distributing the forces either above and/or below the knee joint and away from the patella region. However, a study disclosed in McWalter, et al., "The Effect of Patellar Brace on Three-Dimensional Patellar Kinematics in Patients with Lateral Patellofemoral Osteoarthritis," *Osteoarthritis Cartilage* 19(7):801-808 (2011) concluded that while bracing changed patellar kinematics, the changes in kinematics did not provide a clinically meaningful reduction in pain in the study. Therefore, a need still exists for a device that can effectively manage patellofemoral joint pain and inflammation.

The present invention is directed to overcoming these and other deficiencies in the art.

SUMMARY OF THE INVENTION

One aspect of the present invention relates to a device for managing patellofemoral pain that includes a wearable anchor structure configured to be positioned adjacent to the knee joint of a user. A spring mechanism is attachable, during use, to the anchor structure at first and second attachment positions located laterally and medially of the knee joint, respectively. An attachment component is coupled to the spring mechanism and has an attachment surface configured to be removably attached, during use, to the skin over the patella of the user such that the spring mechanism applies a tension force on the attachment component in an anterior direction.

Another aspect of the invention relates to a method of managing patellofemoral joint pain. The method involves providing the device according to the present invention. The wearable anchor structure is positioned adjacent to the knee joint of the user. The spring mechanism is attached to the anchor structure at first and second attachment positions located laterally and medially of the knee joint. The attachment surface of the attachment component is attached to the skin over the patella of the user. The spring mechanism is connected to the attachment component to apply a tension force on the attachment component in an anterior direction.

A further aspect of the present invention relates to a method of managing patellofemoral joint pain. The method includes applying a prosthetic device about the knee of a user to apply a traction force anteriorly to displace the patella, thereby managing patellofemoral joint pain.

Another aspect of the present invention relates to a subcomponent of the device, which includes an attachment surface configured to be removably attached, during use, to the skin over the patella of a user; and an attachment component connected to the attachment surface, the attachment component being configured for releasably coupling to a spring mechanism such that the spring mechanism, during use, applies a tension force on the attachment component in an anterior direction.

A still further aspect of the invention relates to a method of realigning a user's patella. The method includes applying a prosthetic device about the knee of a user having a mis-aligned patella to apply a traction force anteriorly to displace the patella. The applying of the traction force anteriorly to displace the patella is carried out repeatedly and periodically over a period of time to cause a realignment of the patella by increasing the space between the patella and the femur.

Yet another aspect of the invention relates to a patellofemoral pain management kit. The kit includes a wearable anchor structure, or more than one such anchor structures, configured to be positioned adjacent to the knee joint of a user. The kit further includes a plurality of spring mechanisms having different gauges. Each of the plurality of spring mechanisms is configured to be attached to the anchor structure at first and second attachment positions located laterally and medially of the knee joint, respectively. An attachment component is configured to be coupled to one of the plurality of spring mechanisms. The attachment component has an attachment surface configured to be removably attached, during use, to the skin over the patella of the user such that one of the plurality of spring mechanisms (to which the attachment component is attached) applies a tension force on the attachment component in an anterior direction. Because multiple spring mechanisms are provided, a user may select one of the spring mechanisms that best serves the needs of the user.

The devices and methods of the present invention are designed to help compensate for the loss of cartilage and the associated loss of space for the patella to track easily in the trochlear groove to manage knee pain associated with patellofemoral arthritis. The devices and methods of the present invention are also designed to help alleviate pain associated with patellofemoral pain syndrome, patellar tendonitis, chondromalacia, and patella maltracking, by way of example. Specifically, the patella is advantageously pulled anteriorly throughout the full range of motion during knee flexion. By pulling anteriorly on the patella some of the space lost due to the loss of cartilage is restored, allowing the patella to track more easily and naturally in the trochlear groove. Allowing the patella to track more naturally in the trochlear groove serves to reduce and/or eliminate knee pain associated with patellofemoral arthritis both during activities involving flexion of the knee joint, as well as after such activities. The improved tracking of the patella also reduces and/or eliminates patellofemoral pain and inflammation associated with patellofemoral pain syndrome, patellar tendonitis, chondromalacia, and patella maltracking.

For purposes of this disclosure, the term "about" means ±10%, ±5%, ±4%, ±3%, ±2%, or ±1%, when used to modify force, distance, angles, or any other stated values.

DETAILED DESCRIPTION OF THE INVENTION

The present invention relates to a device for managing patellofemoral pain, methods for managing patellofemoral pain and re-aligning the patella, and a patellofemoral pain management kit. The device and methods of the present invention advantageously pull the skin above the user's patella, and thus the patella, anteriorly throughout the full range of motion during flexion of the knee joint. By pulling anteriorly on the patella, space lost due to the loss of cartilage is restored, allowing the patella to track more easily and naturally in the trochlear groove to allow the user to reduce and/or eliminate patellofemoral pain caused, for example, by knee osteoarthritis.

One aspect of the present invention relates to a device for managing patellofemoral pain that includes a wearable anchor structure(s) configured to be positioned adjacent to the knee joint of a user. A spring mechanism is attachable, during use, to the anchor structure at first and second attachment positions located laterally and medially of the knee joint, respectively. An attachment component is coupled to the spring mechanism and has an attachment surface configured to be removably attached, during use, to the skin over the patella of the user such that the spring mechanism applies a tension force on the attachment component in an anterior direction.

Several embodiments of a device for managing patellofemoral pain are illustrated in FIGS. 1-10. The device may be worn by a user to manage patellofemoral pain caused by, for example, knee osteoarthritis, or more specifically patellofemoral osteoarthritis, patellofemoral pain syndrome, patellar tendonitis, chondromalacia, and/or patella maltracking.

The device may be worn by the user during any activities that involve flexion of the knee joint, such as, by way of example only, running, biking, walking, hiking, etc. Further, if desired, the device can be worn during all waking hours and removed only for sleeping and daily hygiene. For purposes of this disclosure, managing patellofemoral pain means reducing or completely eliminating patellofemoral pain either during such activities or following the completion of such activities.

Figure 1:
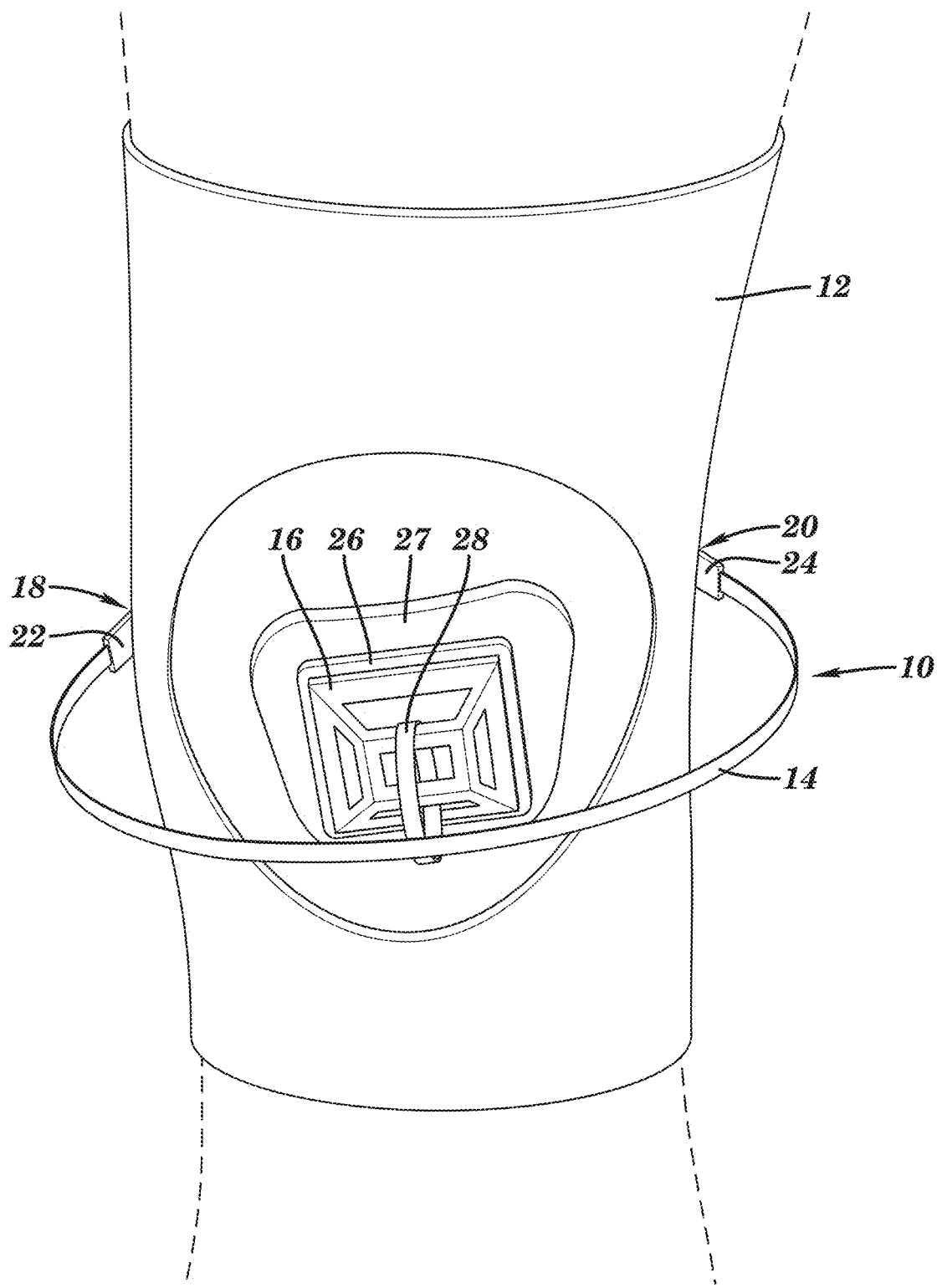
FIG. 1 is a front perspective view of an exemplary device for managing patellofemoral pain in accordance with the present invention, in use.
Figure 2:
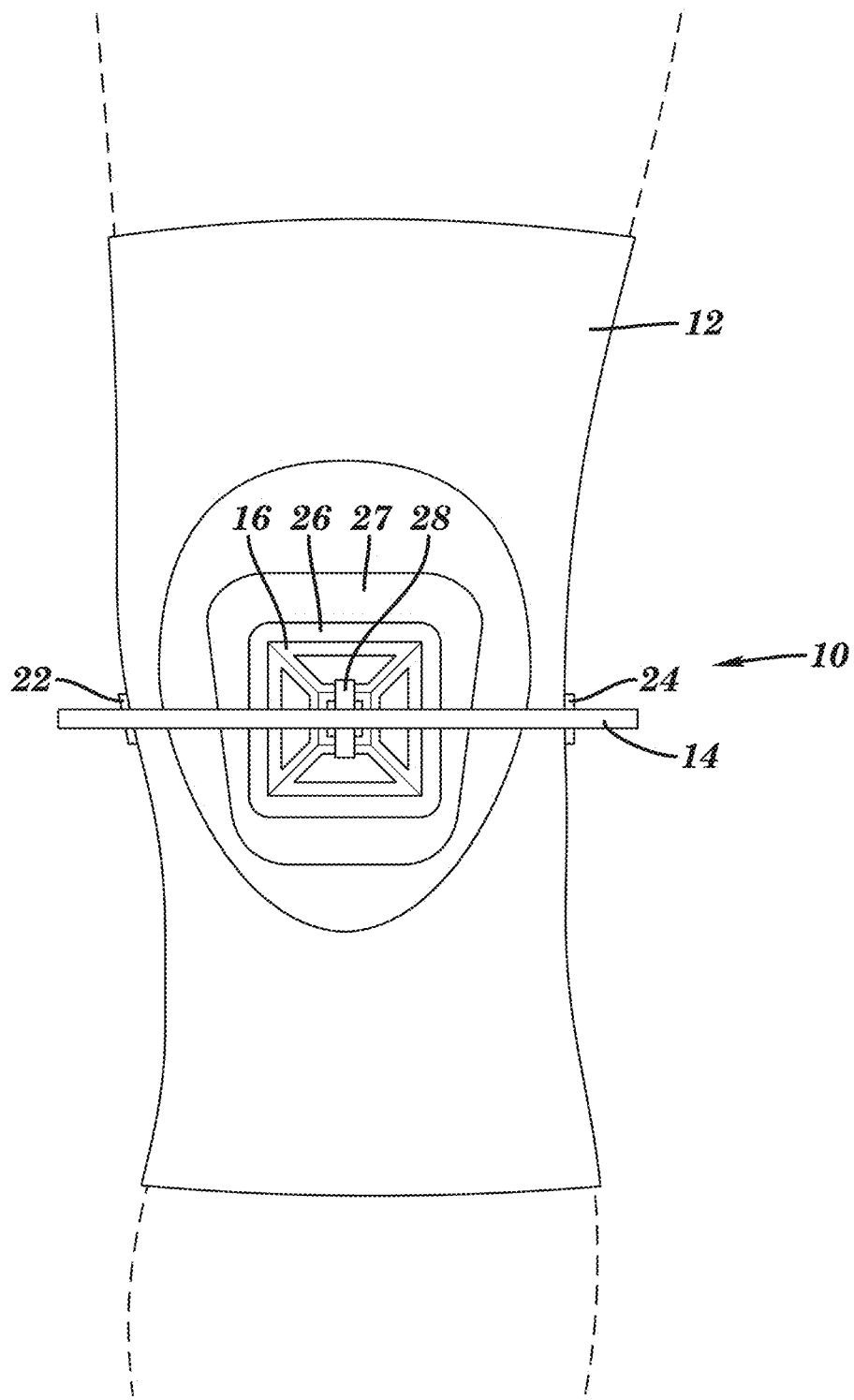
FIG. 2 is a front view of the exemplary device for managing patellofemoral pain in accordance with the present invention, in use.
Figure 3:
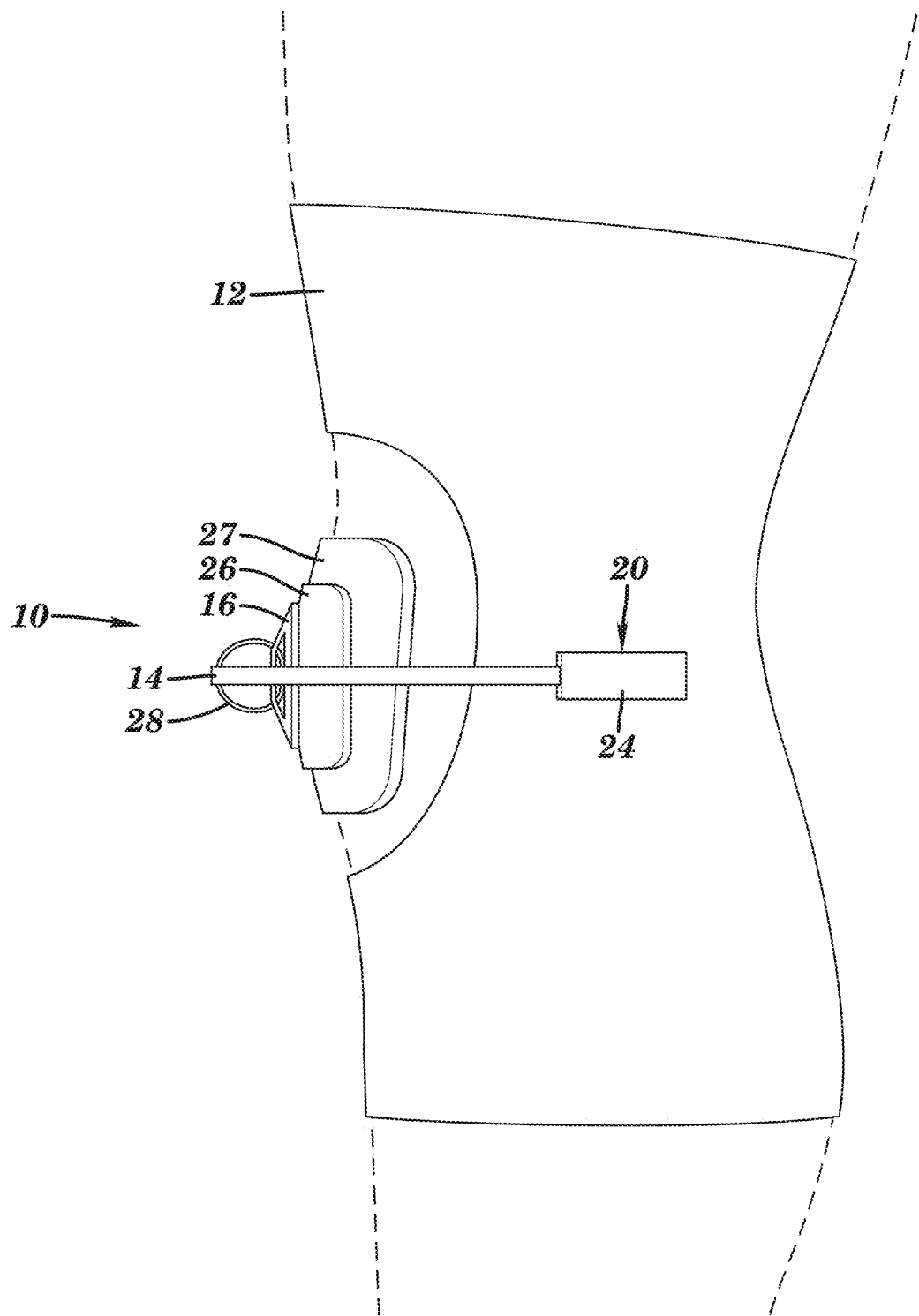
FIG. 3 is a side view of the exemplary device for managing patellofemoral pain in accordance with the present invention, in use.

Referring now more specifically to FIGS. 1-3, the device 10 includes a wearable anchor structure 12, a spring mechanism 14, and an attachment component 16, although device 10 may include other elements in other combinations. Wearable anchor structure 12 is configured to be worn by the user such that it is positioned adjacent to the user's knee joint. In this embodiment, wearable anchor structure 12 is a knee sleeve that is configured to be worn about the user's knee joint with the skin above the patella fully exposed as shown in FIGS. 1-3, although other wearable structures such as knee wraps or other structures wearable about the user's knee joint may be utilized for wearable anchor structure 12.

Wearable anchor structure 12 provides anchoring positions, such as through medial and lateral connectors, on the medial and lateral sides of the user's knee joint, in use, for spring mechanism 14 as described below. However, wearable anchor structure 12 does not need to provide support to the user's knee joint. Providing structural support to the user's knee joint via wearable structure 12 is optional. Accordingly, any suitable configuration that provides the necessary attachment anchoring positions for spring mechanism 14 (with the skin above the user's patella fully exposed for attachment of attachment component 16, as described below) may be utilized.

In one example, wearable anchor structure 12, such as a knee sleeve or wrap, has both a medial connector (not shown) located on the medial side of the user's knee, in use, and a lateral connector (not shown) located on the lateral side of the user's knee, in use. The medial and lateral connectors are located on wearable anchor structure 12 to provide a removable mating attachment of spring mechanism 14 as described below, although in other examples spring mechanism 14 may be coupled to wearable anchor structure in a non-removable attachment.

In one embodiment, the medial connector and the lateral connectors are hook or loop fasteners located on the medial and lateral sides of wearable anchor structure 12 for mating with corresponding hook or loop fasteners located on spring mechanism 14, although the medial and lateral connectors can be any structure configured to provide a mating attachment of spring mechanism 14 to wearable anchor structure 12, such as male or female snap-fit connectors, by way of example only. Regardless of the structure and manner of operation, the medial and lateral connectors that are connected to wearable anchor structure 12 can be permanently secured by mechanical (e.g., sewing) or adhesive attachment of a backing material, or the connector body itself, onto the material that forms wearable anchor structure 12. The medial and lateral connectors may, by way of example, be located approximately at the midpoint of wearable anchor structure 12 along the direction of the user's leg when in use. In another example, wearable anchor structure 12 has multiple medial and lateral connectors located at different positions to allow a user to adjust either the angle of spring mechanism 14 with respect to the user's patella, in use, and/or to adjust the length of spring mechanism 14 to adjust the tension force applied by spring mechanism 14 on attachment component 16 as described below.

Spring mechanism 14 is attachable, during use, to wearable anchor structure 12 at a first attachment position 18 located on the lateral side of the user's knee joint and a second attachment position 20 located on the medial side of the user the user's knee joint. The removable attachment of spring mechanism 14 allows for device 10 to be adjustable by the user to provide the desired tension force on the skin above the user's patella as described in further detail below. First attachment position 18 and second attachment position 20 may be varied, by way of example by having different medial and lateral connectors located on wearable anchor structure 12, or by having a plurality of connectors on spring mechanism 14, or both. Adjustment of the attachment position allows a user to adjust the tension force of spring mechanism 14 on attachment component 16 or the angle at which spring mechanism 14 rests with respect to the user's patella. Spring mechanism 14 is sized and configured such that, during use, spring mechanism 14 is spaced apart from the user and wearable anchor structure 12 along its length between first attachment position 18 and attachment component 16, and between attachment component 16 and second attachment position 20.

Figure 4:
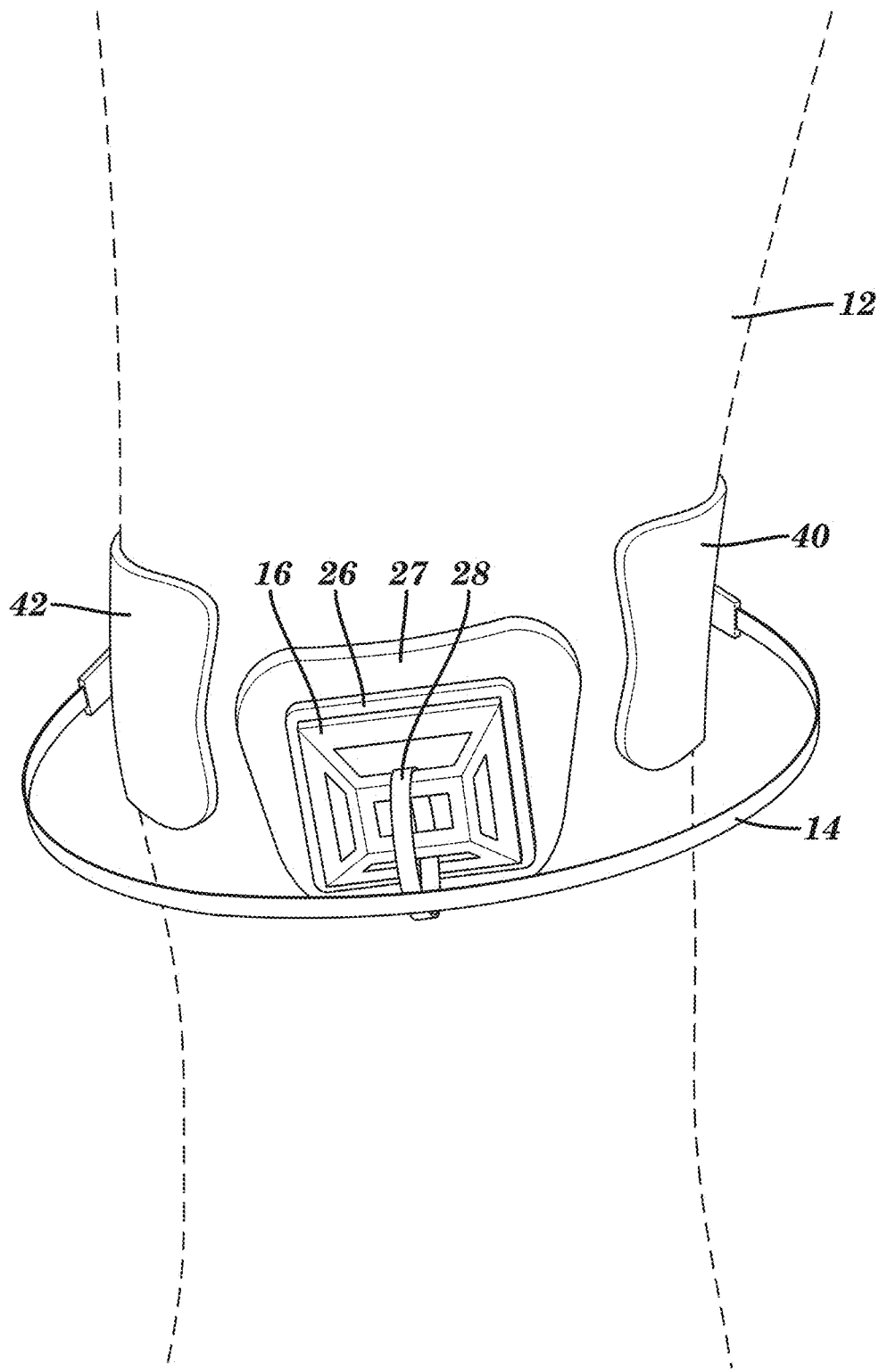
FIG. 4 is front perspective view of the exemplary device for managing patellofemoral pain with another exemplary wearable anchor structure, in use.

In another embodiment, as shown in FIG. 4, the wearable anchor structure 12 may be made up of multiple components, such as a medial anchor member 40 and a lateral anchor member 42 configured to provide the necessary anchoring positions at the medial and lateral sides of the user's knee, respectively, for spring mechanism 14. Each anchor member 40 and 42 includes an adhesive layer and a connector of the type described above (e.g., hook or loop fastener, or male or female snap connectors). The adhesive layer of medial anchor member 40 allows a user to adhere medial anchor member 40 to the skin located medially of the knee joint, and the adhesive layer of the lateral anchor member 42 allows a user to adhere lateral anchor member 42 to the skin located laterally of the knee joint. The anchor members 40 and 42 can be formed, by way of example, by securing the connectors mechanically or adhesively to a piece of kinesiology tape, or by providing each connector with an integral adhesive layer. Regardless of the specific embodiment, where adhesive layers are used to attach anchor members 40 and 42 to a user's skin, anchor members 40 and 42 are preferably provided with a release layer that protects the adhesive layer prior to its use.

Figure 5:
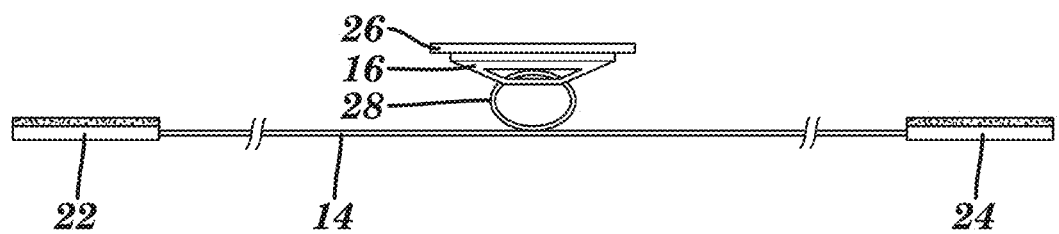
FIG. 5 is a top view of the spring mechanism and attachment component of the exemplary device for managing patellofemoral pain in accordance with the present invention.
Figure 6:
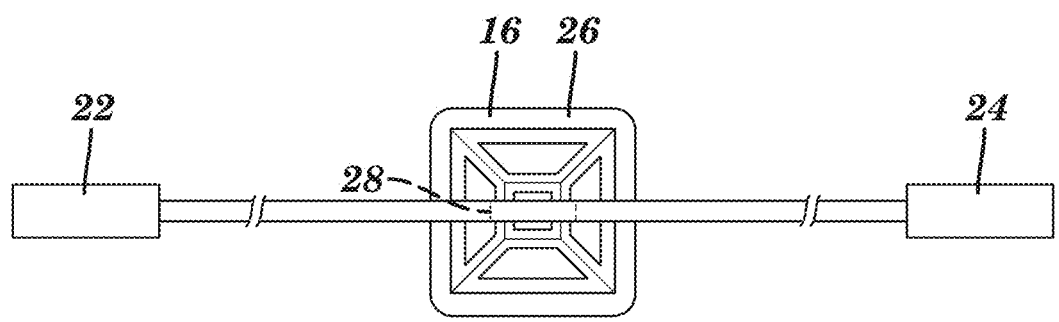
FIG. 6 is a front view of the spring mechanism and attachment component of the exemplary device for managing patellofemoral pain in accordance with the present invention.

Referring now more specifically to FIGS. 5 and 6, in one example, spring mechanism 14 includes a first connector 22 and a second connector 24, such as hook or loop fasteners, located at opposing ends thereof. The first connector 22 and second connector 24 matingly engage with the lateral and medial connectors, which in this example are corresponding hook or loop fasteners, on wearable anchor structure 12 or on the anchor members 40 and 42. In other examples, first connector 22 and second connector 24 may be male or female snap fit connectors, or any other types of connectors known in the art that allow for a mating engagement between the medial and lateral connectors on wearable anchor structure 12; or on the anchor members 40 and 42. In one example, spring mechanism 14 has multiple first connectors 22 and/or multiple second connectors 24 (along the length of spring mechanism 14) that allow for the length of spring mechanism 14, and thus the tension force applied, to be adjusted by the user.

Referring again more specifically to FIGS. 1-3, when attached during use, spring mechanism 14 passes anterior to the user's patella at roughly its midline, although the angle of spring mechanism 14 may be adjusted, such as by using medial and lateral connectors located at different locations on wearable anchor structure 12 (or the user's placement of anchor members 40 and 42 at different heights next to the knee joint), to apply the tension force supplied by spring mechanism 14 at various angles. Spring mechanism 14 is sized and configured such that, during use, spring mechanism 14 is spaced apart from the user and wearable anchor structure 12 along its length between first attachment position 18 and attachment component 16, and between attachment component 16 and second attachment position 20. In this example, spring element 14 is configured with a length such that, in use, i.e., when spring mechanism 14 is coupled to wearable anchor structure 12, there is a space between spring mechanism 14 and attachment component of about 0.1 inches (2.54 mm) to about 3.0 inches (76.2 mm), although in other examples the space may be about 0.125 inches (3.175 mm) to about 2.875 inches 73.025 mm), about 0.15 inches (3.81 mm) to about 2.75 inches (69.85 mm), about 0.25 inches (6.35 mm) to about 2.75 inches (69.85 mm), or about 0.30 inches (7.62 mm) to about 2.25 inches (57.15 mm).

In this example, spring mechanism 14 is a flexible strip, such as a plastic rod, although other materials, such as metal-coated plastics, metals, or other flexible materials may be utilized as spring mechanism 14. The material and gauge or thickness of spring mechanism 14 may be varied depending on the desired amount of tension to be provided by spring mechanism 14 on attachment component 16. In one example, spring mechanism 14 has an adjustable length that allows the tension supplied by spring mechanism 14 to be adjusted by the user. By way of example, spring mechanism 14 may include an adjustment mechanism, such as employed in zip ties by way of example only, to allow the length of spring mechanism 14 to be adjusted by the user while spring mechanism 14 is attached to wearable anchor structure 12.

Attachment component 16 is coupled to spring mechanism 14. In one example, attachment component 16 is releasably attached to spring mechanism 14, although a permanent coupling between spring mechanism 14 and attachment component 16 may be utilized in other examples. Releasable (or adjustable) coupling between attachment component 16 and spring mechanism 14 can be achieved using a removable linkage. In one embodiment, spacer element 28 can be in the form of a split ring that allows spacer element 28 to be decoupled from attachment component 16 and/or spring mechanism 14. Permanent couplings will depend on the materials used, and may include adhesives, sonic welding, arc welding, rivets, links, or the like. In this example, a spacer element 28, such as a plastic loop structure, couples attachment component 16 to spring mechanism 14. Spacer element 28 may be adjustable in length, such as through a zip tie configuration, which allows for the length of spacer element 28 to be adjusted to alter the spacing or distance between spring mechanism 14 and attachment component 16 to adjust the tension force supplied by spring mechanism 14 on attachment component 16. Spacer element 28 is configured with a length such that, in use, i.e., when spring mechanism 14 is coupled to wearable anchor structure 12, there is a space between spring mechanism 14 and attachment component 16 of about 0.1 inches (2.54 mm) to about 3.0 inches (76.2 mm), although in other examples the space may be about 0.125 inches (3.175 mm) to about 2.875 inches 73.025 mm), about 0.15 inches (3.81 mm) to about 2.75 inches (69.85 mm), about 0.25 inches (6.35 mm) to about 2.75 inches (69.85 mm), or about 0.30 inches (7.62 mm) to about 2.25 inches (57.15 mm).

When the coupling between spacer element 28 and spring mechanism 14 is adjustable, that adjustability may allow the location of the connection between spacer element 28 and spring mechanism 14 to be moved along the length of spring mechanism 14 to adjust the angle at which the tension force supplied by spring mechanism 14 is applied to attachment component 16. Adjustability can be achieved using, e.g., a pair of resilient O-rings that can be moved along the length of spring mechanism 14 to facilitate maintenance of a desired angular tension of spring mechanism 14 on attachment component 16. By way of example, changing the attachment location of spacer element 28 along the length of spring mechanism 14 changes the angle at which spring mechanism 14 is pulled in the anterior direction along the horizontal plane of spring mechanism 14 extending between the medial side of the user's knee and the lateral side of the user's knee. The angle at which spring mechanism 14 is pulled in this example may be from 90 degrees (straight out or directly anterior to the user's patella) to 0 degrees (i.e., directly lateral to the user's patella) or 180 degrees (i.e. directly medial to the user's patella).

For some conditions it may be advantageous to have the pulling force of spring mechanism 14 close to directly anterior to the user's patella such that the angle is between about 45 degrees (extending toward the lateral side of the user's knee) to about 135 degrees (extending toward the medial side of the user's knee), although in other examples the angle may be from about 55 degrees to about 125 degrees, about 65 degrees to about 115 degrees, about 75 degrees to about 105 degrees, or about 80 degrees to about 100 degrees. For other conditions, it may be desirable to have the tension force applied between about 0 degrees to about 45 degrees in the lateral direction, or about 135 degrees to about 180 degrees in the medial direction.

As illustrated in FIGS. 1-4 and FIGS. 5-6, spacer element 28 can be aligned in any orientation (e.g., the vertical and horizontal orientations shown).

Figure 7A:
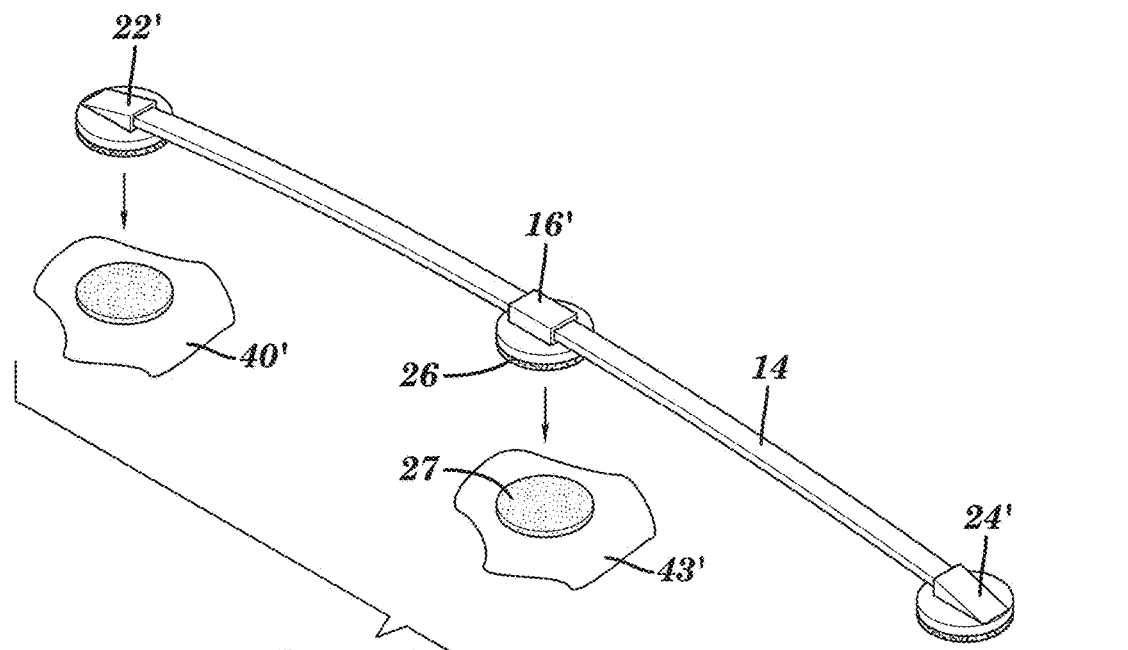
FIG. 7A is a perspective view of another exemplary spring mechanism and attachment component configuration that may be used with the exemplary device for managing patellofemoral pain in accordance with the present invention.
Figure 7B:
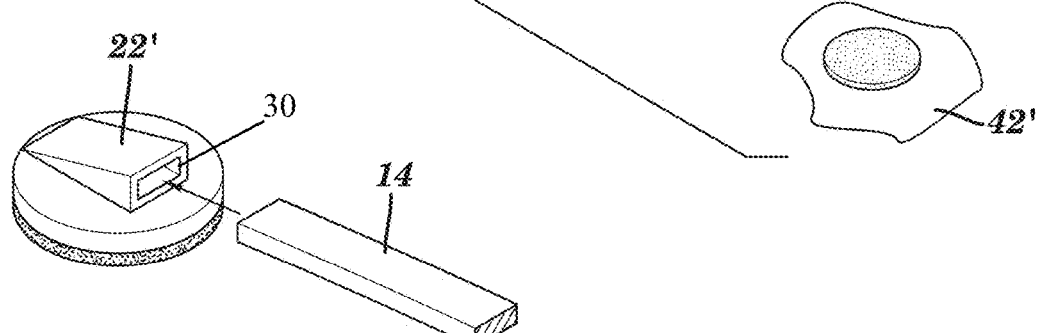
FIG. 7B is a perspective view of one the connectors utilized in FIG. 7A.
Figure 7C:
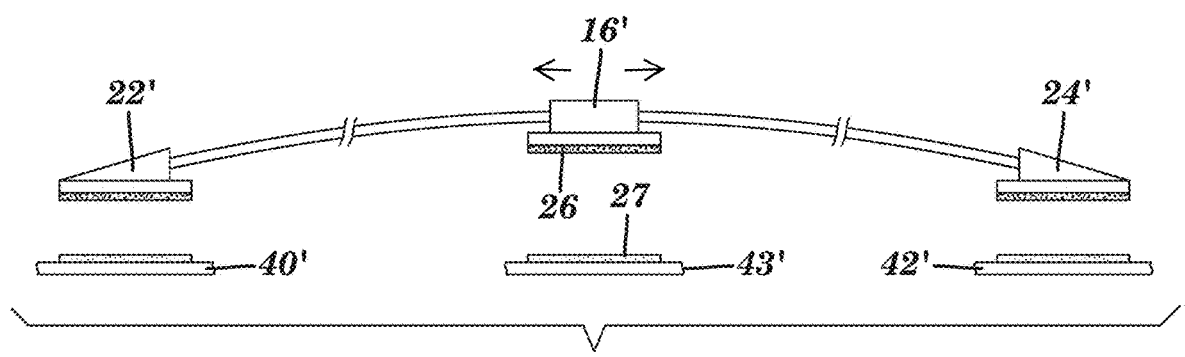
FIG. 7C is a side elevation view of the exemplary spring mechanism shown in FIG. 7A.

In another example, as shown in FIGS. 7A-7C, spring mechanism 14 is attached directly to attachment component 16' without the use of spacer element 28. By way of example, attachment component 16', first connector 22', and second connector 24' may have one or more slots 30 located on a surface thereof configured to receive spring mechanism 14, although other configurations that allow direct attachment of spring mechanism to attachment component 16' may be utilized. In this embodiment, attachment component 16', first connector 22', and second connector 24' (including integral slots 30) are formed using 3D printing techniques, although other manufacturing techniques, such as molding may be utilized. In one example, the slots 30 or other configuration on attachment component 16' for receiving spring mechanism 14 may be molded as part of attachment component 16', first connector 22', and second connector 24'. By inserting spring mechanism 14 through the slot of attachment component 16' with adhesives applied to a portion of spring mechanism 14, spring mechanism 14 and attachment component 16' can be permanently connected. Alternatively, other direct attachment mechanisms, such as hook and loop fasteners or other mating fasteners, may be utilized to attach spring mechanism 14 directly to attachment component 16', first connector 22', and second connector 24'. Spring mechanism 14 may be press fit into slots 30, although in other examples, spring mechanism 14 may be welded or adhesively secured in slots 30. In contrast to the embodiment of FIGS. 1-6 containing the spacer element 28, which promotes a space between spring mechanism 14 and attachment component 16, the embodiment of FIGS. 7A-7C lacks spacing between spring mechanism 14 and attachment component 16'.

In certain embodiments, spring mechanism 14 can slide through slot 30 of attachment component 16', but the ends of spring mechanism 14 can be permanently attached to first and second connectors 22', 24'. This allows some free movement of spring mechanism 14 without causing angular adjustment of the tension in the anterior direction.

As shown in FIGS. 7A and 7C, connectors 22' and 24' are configured to be coupled to corresponding anchor members 40' and 42', while attachment component 16' is configured to be coupled anchor member 43'. Each of attachment component 16' and connectors 22' and 24' includes a fastener that is designed to mate with a corresponding fastener (e.g., a hook and loop fastener) on anchor members 40', 42', and 43'. In this example, anchor members 40', 42', and 43' provide the wearable anchor structure. Each anchor member 40', 42', and 43' includes an adhesive layer and a connector of the type described above (e.g., hook or loop fastener, or male or female snap connectors). The adhesive layer of medial anchor member 40' allows a user to adhere medial anchor member 40' to the skin located medially of the knee joint, and the adhesive layer of the lateral anchor member 42' allows a user to adhere lateral anchor member 42' to the skin located laterally of the knee joint. Anchor member 43' can be adhered to this skin over the user's patella. The anchor members 40', 42', and 43' can be formed, by way of example, by securing the connectors mechanically or adhesively to a piece of kinesiology tape, or by providing each connector with an integral adhesive layer. Regardless of the specific embodiment, where adhesive layers are used to attach anchor members 40', 42' and 43' to a user's skin, anchor members 40', 42', and 43' are preferably provided with a release layer that protects the adhesive layer prior to its use.

In one example, spring mechanism 14 is positioned such that it extends in a horizontal plane directly perpendicular to a plane defined by a surface of the user's patella. In another example, spring mechanism 14 is adjustable to have a slight incline or decline with respect to the horizontal plane. By way of example, spring mechanism may be inclined or declined about ±15% from the horizontal plane. In other examples, the angle is about ±10%, ±7%, ±4%, or ±1%.

In another example, spring mechanism 14 is attached to attachment component 16 using a threaded screw, although other adjustable attachment mechanisms may be utilized. The threaded screw can be received within a threaded shaft on attachment component 16, with the screw head engaged by spring mechanism 14 (with the threaded screw passing through an opening in spring mechanism 14). In this example, the position and length of the threaded screw determines a distance between spring mechanism 14 and attachment component 16 to adjust the tension force supplied on attachment component 16 by spring mechanism 14. This configuration advantageously provides a user adjustment of the tension force supplied by spring mechanism 14 during use of device 10.

Attachment component 16 may have any configuration suitable for attachment to the skin above the user's patella. Attachment component 16 includes an attachment surface 26 configured to be removably attached, during use, to the skin over the user's patella. Attachment of the attachment component 16, through the attachment surface 26, allows spring mechanism 14 to apply a tension force on attachment component 16 in an anterior direction with respect to the user's knee.

In one example, attachment surface 26 may be a hook or loop fastener that may be coupled to a corresponding hook or loop fastener placed over the skin of the user's patella on a corresponding attachment surface 27. By way of example, the corresponding hook or loop fastener may be adhesively attached to corresponding attachment surface 27, which is an adhesive layer, such as kinesiology tape, that may be applied directly to the skin above the user's patella as illustrated in FIGS. 1-3. In another example, attachment surface 26 is an adhesive layer that may be applied directly the skin above the user's patella without the use of corresponding attachment surface 27. In one example, attachment component 16 may be formed of a flexible material configured to closely adhere to the skin above the user's patella, although other configurations for attachment component 16 can be employed. When attachment component 16 is attached to the skin above the user's patella, the attachment component 16 pulls spring mechanism 14 toward the user's knee joint, creating a tension force in the opposition direction, i.e., anterior to the user's knee joint.

Figure 8A:
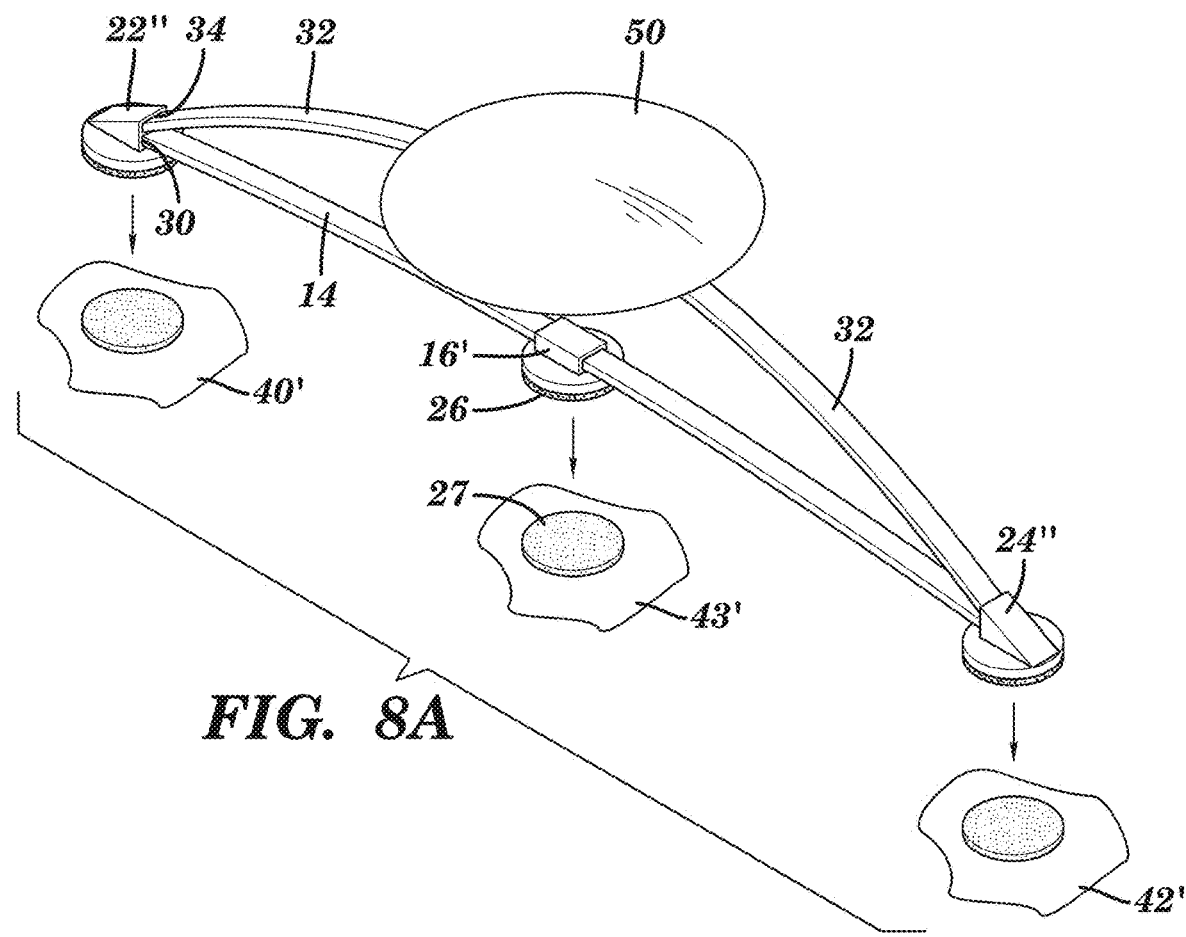
FIG. 8A is a perspective view of the exemplary spring mechanism and attachment component shown in FIG. 7 with an additional shield component attached thereto.
Figure 8B:
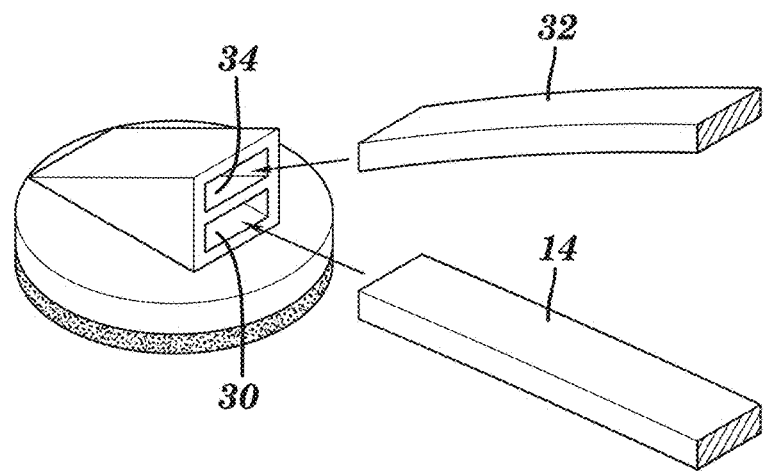
FIG. 8B is a perspective view of one of the connectors utilized in FIG. 8A.

Referring now to FIGS. 8A and 8B, in one example the device 10 also includes an optional shield component 50 coupled to first connector 22" and second connector 24" through arms 32 that can be inserted in additional slots 34 as shown in FIG. 8B, although other configurations can be employed. Arms 32 can be adhesively secured or welded within slots 34. Alternatively, arms 32 may be press fit into slots 34 during use for removable attachment for optional use of shield component 50. Shield component 50 provides a dome-shaped protective element for device 10 when device 10 is utilized with longer pants. Shield component 50 is configured to cover attachment mechanism 16' to shield the attachment mechanism 16' and underlying spring mechanism 14 from contact with the user's clothing, which provides a more secure attachment when the user wears long pants during use of device 10. Shield component 50 may be formed using 3D printing techniques, although other manufacturing techniques, such as molding, may be employed.

Figure 9:
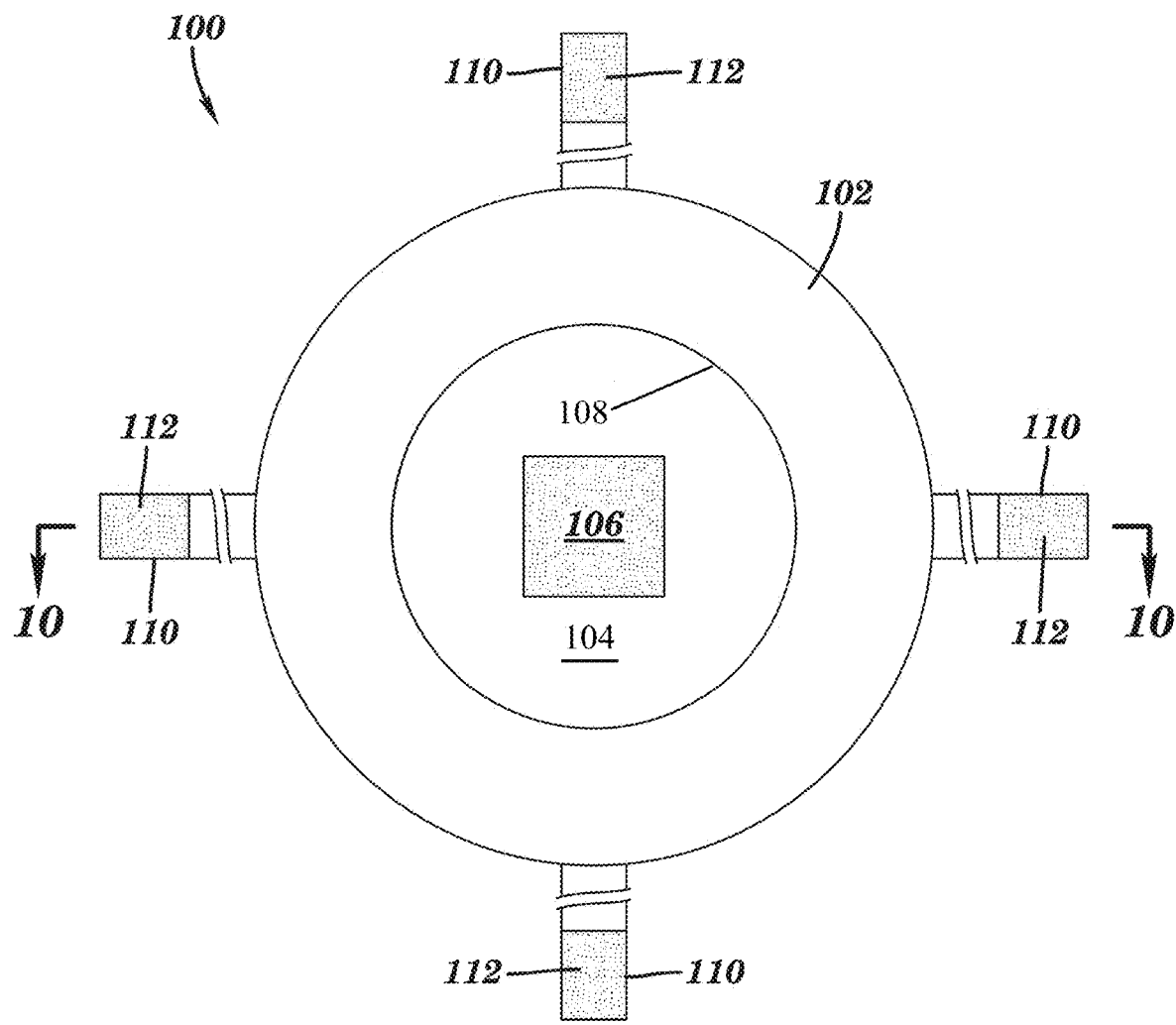
FIG. 9 is a bottom view of another exemplary device for managing patellofemoral pain in accordance with the present invention.
Figure 10:
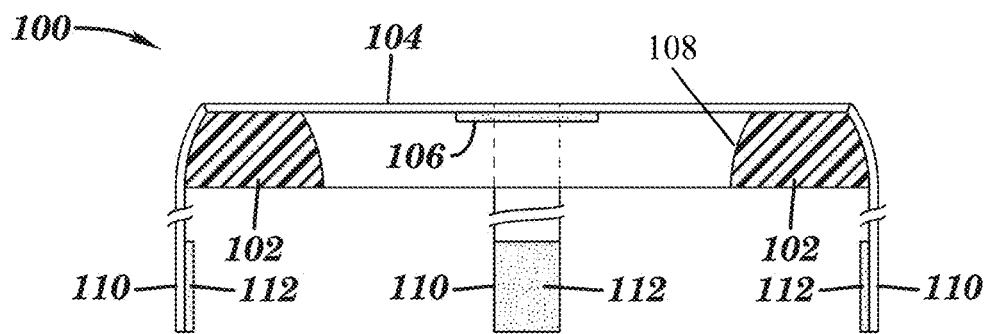
FIG. 10 is a side cross section view of the exemplary device for managing patellofemoral pain shown in FIG. 9.

Another embodiment of a device 100 for managing patellofemoral pain is illustrated in FIGS. 9 and 10. Device 100 is the same in operation as device 10 and is configured to provide a tension force on the user's patella in an anterior direction during use. Device 100 is conducive to being worn under a user's clothing. Device 100 includes a support structure 102, a spring mechanism 104, and an attachment component 106, although device 10 may include other elements in other combinations. Device 100 may be utilized with a wearable support structure, such as wearable support structure 12 described above and shown in FIGS. 1-3.

In this example, support structure 102 is a donut-shaped structure configured with an inner hole 108 that can be placed over the user's patella such that the support structure 102 surrounds the patella during use. In one example, support structure 102 is formed of silicone, although other soft plastics or rubbers may be utilized for support structure 102.

Spring mechanism 104 in this example is a flexible fabric that is located over the support structure. Suitable fabrics have sufficient flexibility to provide the necessary tension force as described below and include, by way of example only, nylon, spandex, elastane, and polyester, as well as blends of those materials. In one example, a moisture wicking flexible fabric may be utilized as spring mechanism 104.

Spring mechanism 104 includes attachment straps 110 that allow spring mechanism 104 to be attached at various locations about the user's patella. Attachment straps 110, in one example, include fasteners 112 such as hook or loop fasteners, located at the ends thereof. The fasteners 112 of the attachment straps 110 matingly engage with connectors on a wearable anchor structure, such as wearable anchor structure 12 or anchor structures 40 and 42 described above. Fasteners 112 may attach to wearable anchor structure above, below, medial, and lateral to the user's patella, although other configurations of fasteners may be utilized. In other examples, fasteners 112 may be male or female snap fit connectors, or any other types of connectors known in the art that allow for a mating engagement of the fasteners 112 to a wearable anchor structure may be employed. Mating engagement of fasteners provides a tension force on spring mechanism 104, which in this example is a flexible fabric, when spring mechanism 104 is located over support structure 102. The amount of tension may be varied based on the location of the engagement of fasteners 112.

Attachment component 106 is coupled to spring mechanism 104. Attachment component 106 is configured for attachment to the skin above the user's patella. Attachment of the attachment component 106 allows spring mechanism 104 to apply a tension force on attachment component 106 in an anterior direction with respect to the user's knee.

In one example, attachment component 106 is a hook or loop fastener that may be coupled to a corresponding hook or loop fastener placed over the skin of the user's patella. By way of example, the corresponding hook or loop fastener may be adhesively attached by an adhesive layer, such as kinesiology tape, that may be applied directly to the skin above the user's patella, such as anchor structure 43'. In another example, attachment component 106 is an adhesive layer that may be applied directly the skin above the user's patella. When attachment component 106 is attached to the skin above the user's patella, the attachment component 106 pulls spring mechanism 104 against support structure 102 and toward the user's knee joint, creating a tension force in the opposition direction, i.e., anterior to the user's knee joint.

Another aspect of the invention relates to a method of managing patellofemoral joint pain. In one embodiment, the method involves applying a prosthetic device about the knee of a user to apply a traction force anteriorly to displace the patella, thereby managing patellofemoral joint pain. During use of the device (i.e., during activities), patellofemoral joint pain is reduced or eliminated due to the anterior traction applied to the patella. This also has the effect of reducing or eliminating post-activity pain and/or swelling, i.e., when the device is no longer being worn. The method involves, by way of example, managing patellofemoral joint pain associated with patellofemoral arthritis, patellofemoral pain syndrome, patellar tendonitis, chondromalacia, and/or patella maltracking.

Use of any of the foregoing embodiments, and variations thereof, are contemplated for applying the anterior traction force.

An exemplary method of managing patellofemoral joint pain involves applying a prosthetic device, such as device 10, about the knee of a user. Any device suitable to provide a traction force to anteriorly displace the user's patella may be utilized. For purposes of this application, displacing the user's patella means applying a traction force that pulls the patella in an anterior direction, preferably throughout the full range of motion during knee flexion to supply a space between the bones of the patella, such that the knee tracks more easily and naturally in the trochlear groove. The anterior pull of the patella compensates for the space lost due to the loss of cartilage due to patellofemoral arthritis. The anterior pull also serves to manage patellofemoral pain related to patellofemoral pain syndrome, patellar tendonitis, chondromalacia, and/or patella maltracking. The anterior pull of the patella through the traction force applied to the skin above the user's patella helps to reduce and/or completely eliminate pain caused by, for example, patellofemoral arthritis, patellofemoral pain syndrome, patellar tendonitis, chondromalacia, and/or patella maltracking.

According to another embodiment, the method involves providing the device according to the present invention. The wearable anchor structure is positioned adjacent to the knee joint of the user. The spring mechanism is attached to the anchor structure at first and second attachment positions located laterally and medially of the knee joint. The attachment surface of the attachment component is attached to the skin over the patella of the user. The spring mechanism is connected to the attachment component to apply a tension force on the attachment component in an anterior direction.

In the various embodiments described herein, spring mechanism 14 or 104 applies a tension force (pound-force) of about 0.05 to about 2 pounds on the corresponding attachment component, which in turn applies the tension force to the skin above the user's patella and the user's patella itself, although the tension force may be between about 0.05 to about 1.5 pounds, about 0.1 to about 1.2 pounds, or about 0.15 to about 1.0 pound. Further, the amount of tension force applied to the skin above the user's patella may vary depending on the positioning of the flexion of the user's knee. Although exemplary tension forces are described, the tension force may be adjusted using one or more of the adjustment techniques disclosed herein. In some examples, the tension force may be about a pound, or higher depending on the material and gauge used for spring mechanism 14 or 104.

A still further aspect of the invention relates to a method of realigning a user's patella. The method includes applying a prosthetic device about the knee of a user having a mis-aligned patella to apply a traction force anteriorly to displace the patella. The applying of the traction force anteriorly to displace the patella is carried out repeatedly and periodically over a period of time to cause a realignment of the patella by increasing the space between the patella and the femur. This re-alignment includes the promotion of an increase in the space between the femur and the patella while wearing the device as well as while not wearing the device (after a period of use). The latter improvement was entirely unexpected. As demonstrated in the accompanying examples, prolonged periodic and/or continuous use of the device affords a surprising therapeutic benefit of causing re-alignment of the patella.

An exemplary method of using device 10 will now be described with reference to FIGS. 1-3. First, wearable anchor structure 12 is positioned adjacent to the knee joint of the user as illustrated in FIG. 1. Next, attachment surface 26 of attachment component 16 is attached to the skin over the user's patella. In one example, attachment surface 26 is an adhesive layer that may be applied directly the skin above the user's patella. In another example, attachment surface 26 may be a hook or loop fastener that may be coupled to a corresponding hook or loop fastener on corresponding attachment surface 27 placed over the skin of the user's patella. By way of example, the corresponding hook or loop fastener may be adhesively attached to corresponding attachment surface 27 that is an adhesive layer, such as kinesiology tape, that may be applied to the skin above the user's patella as illustrated in FIGS. 1-3.

Next, spring mechanism 14 is attached to wearable anchor structure 12 at first attachment position 18 and second attachment position 20 located laterally and medially of the knee joint, respectively, although other attachment positions may be employed to adjust the angle and amount of the tension force supplied by spring mechanism 14. Spring mechanism 14 is then attached to attachment component 16 through spacer element 28. In one embodiment, spacer element 28 may be integrally coupled to spring mechanism 14, although in other embodiments, spacer element 28 can be coupled to attachment component 16 and spring mechanism 14 prior to use.

Referring again to FIG. 1, next, spring mechanism 14 is coupled to the attachment component 16. Spring mechanism 14 is sized and configured such that, during use, spring mechanism 14 is spaced apart from the user and wearable anchor structure 12 along its length between first attachment position 18 and attachment component 16, and between attachment component 16 and second attachment position 20. This configured allows spring mechanism 14 to apply a tension force on attachment component 16 in an anterior direction away from the user's knee joint. Specifically, when attachment component 16 is attached to the skin above the user's patella, the attachment component 16 pulls spring mechanism 14 toward the user's knee joint, creating a tension force in the opposition direction, i.e., anterior to the user's knee joint. The anterior pull of the spring mechanism 14 on the skin above the user's patella serves to displace the user's patella, i.e., move the user's patella in an anterior direction to provide space in the trochlear groove for the patella to move during flexion of the user's knee.

The method may further include providing a number of adjustments to adjust the tension force supplied. In one example, first attachment position 18 and second attachment position 20 as shown in FIG. 1 are altered to adjust the tension force on attachment component 16 as described above. In another example, a length of spring mechanism 14, such as through the use of an adjustment mechanism such as a zip tie type structure, is changed to adjust the tension force on attachment component 16. In yet another example, the gauge of spring mechanism 14 may be altered to adjust the tension.

In yet another example, spring mechanism 14 may be coupled to attachment device 16 by a threaded screw. In this example, the position of the screw is adjustable to determine the distance between spring mechanism 14 and attachment component 16 to adjust the tension force on attachment component 16.

In a further example, as shown in FIG. 1, spacer element 28 couples attachment component 16 to spring mechanism 14. The method further includes adjusting spacer element 28 with respect to spring mechanism 14 to adjust a distance between spring mechanism 14 and attachment component 16, as described above, to adjust the tension force on attachment component 16. In this example, the method further includes adjusting the positioning of the coupling between spacer element 28 and spring mechanism 14 along the length of spring mechanism 14 to adjust the angle of the tension force in the anterior direction on attachment component 16 as described above.

Another exemplary method of using device 10 will now be described with reference to FIGS. 4-6. This exemplary method is the same as the exemplary method described with reference to FIGS. 1-3 except as described below. In this embodiment, wearable anchor structure 12 is made up of a number of components including medial anchor member 40 and lateral anchor member 42 configured to provide the necessary anchoring positions at the medial and lateral sides of the user's knee, respectively, for spring mechanism 14. First, wearable anchor structure 12 is positioned adjacent to the knee joint of the user as illustrated in FIG. 4 by placing medial anchor member 40 at the medial side of the user's knee and lateral anchor member 42 is located on the lateral side of the user's knee Next, attachment surface 26 of attachment component 16 is attached to the skin over the user's patella. In one example, attachment surface 26 is an adhesive layer that may be applied directly the skin above the user's patella. In another example, attachment surface 26 may be a hook or loop fastener that may be coupled to a corresponding hook or loop fastener on corresponding attachment surface 27 placed over the skin of the user's patella. By way of example, the corresponding hook or loop fastener may be adhesively attached to corresponding attachment surface 27 that is an adhesive layer, such as kinesiology tape, that may be applied to the skin above the user's patella as illustrated in FIG. 4.

Next, spring mechanism 14 is attached to medial anchor member 40 and lateral anchor member 42 laterally and medially of the knee joint, respectively, although other attachment positions may be employed to adjust the angle and amount of the tension force supplied by spring mechanism 14. Spring mechanism 14 is then attached to attachment component 16 through spacer element 28. In one embodiment, spacer element 28 may be integrally coupled to spring mechanism 14, although in other embodiments, spacer element 28 can be coupled to attachment component 16 and spring mechanism 14 prior to use.

Referring again to FIG. 4, spring mechanism 14 is coupled to the attachment component 16 (through spacer 28) to apply a tension force on attachment component 16 in an anterior direction away from the user's knee joint. Specifically, when attachment component 16 is attached to the skin above the user's patella, the attachment component 16 pulls spring mechanism 14 toward the user's knee joint, creating a tension force in the opposition direction, i.e., anterior to the user's knee joint. The anterior pull of the spring mechanism 14 on the skin above the user's patella serves to displace the user's patella, i.e., move the user's patella in an anterior direction to provide space in the trochlear groove for the patella to move during flexion of the user's knee.

The method may further include providing a number of adjustments to adjust the tension force supplied as described with respect to FIGS. 1-3 above.

Yet another exemplary method of using device 10 will now be described with reference to FIGS. 7A-7C. This exemplary method is the same as the exemplary method described with reference to FIGS. 1-3 except as described below. First, a wearable anchor structure is positioned adjacent to the knee joint of the user as illustrated in either FIG. 1 or FIG. 4. As shown in FIGS. 7A and 7C, the wearable anchor structure includes anchor members 40', 42', and 43'. Next, first connector 22' and second connector 24' are attached to anchor members 40' and 42' on the lateral and medial sides of the user's knee, respectively.

Next, attachment surface 26 of attachment component 16' is attached to attachment surface 27 on anchor member 43'. Attachment surface 26 may be a hook or loop fastener that may be coupled to a corresponding hook or loop fastener on corresponding attachment surface 27 on anchor member 43' placed over the skin of the user's patella. When attachment component 16' is attached to anchor member 43', which is located over the user's patella, the attachment component 16' pulls spring mechanism 14 toward the user's knee joint, creating a tension force in the opposition direction, i.e., anterior to the user's knee joint. The anterior pull of the spring mechanism 14 on the skin above the user's patella serves to displace the user's patella, i.e., move the user's patella in an anterior direction to provide space in the trochlear groove for the patella to move during flexion of the user's knee.

In another embodiment, first connector 22" and second connector 24" as shown in FIG. 8A may be utilized. In this embodiment, the method further includes providing optional shield component 50 above the attachment component 16' in the anterior direction from the user's knee to provide a protective cover for attachment component 16'. Shield component 50 may be optionally employed when the user is wearing long pants and is removable to allow for optional use of shield component 50. Shield component 50 is coupled to first connector 22" and second connector 24" by inserting arms 32 into the slots 34 located on both first connector 22" and second connector 24" (as shown in FIG. 8B).

An exemplary method of using device 100 will now be described with reference to FIGS. 9 and 10. This exemplary method is the same as the exemplary method described with reference to FIGS. 1-3 except as described below. First, wearable anchor structure 12 is positioned adjacent to the knee joint of the user as illustrated in either FIG. 1 or FIG.

4. In this embodiment, wearable anchor structure 12 includes additional attachment points for spring mechanism 104 located above and below the user's knee. Support structure 102 is placed over the user's patella such that support structure 102 surrounds the user's patella. Spring mechanism 104, which in this embodiment is a flexible fabric, is placed over support structure 102 and coupled to wearable anchor structure 12 through attachment straps 110 and fasteners 112 using a mating engagement, such as through hook and loop fastening for example. Mating engagement of fasteners 112 to wearable anchor structure 12 provides a tension force on spring mechanism 104. Although four fasteners 112 are illustrated, other numbers of fasteners, such as fasteners medial and lateral to the user's patella, may be employed. The amount of tension may be varied based on the location of the engagement of fasteners 112 on wearable anchor structure 12.

Next, attachment component 106 is attached to the skin over the user's patella. The anterior pull of the spring mechanism 104 on the skin above the user's patella serves to displace the user's patella, i.e., move the user's patella in an anterior direction to provide space in the trochlear groove for the patella to move during flexion of the user's knee.

Yet another aspect of the invention relates to a patellofemoral pain management kit. The kit includes a wearable anchor structure (or more than one such anchor structure) configured to be positioned adjacent to the knee joint of a user. The kit further includes a plurality of spring mechanisms having different gauges. Each of the plurality of spring mechanisms are configured to be attached to the anchor structure(s) at first and second attachment positions located laterally and medially of the knee joint, respectively. An attachment component is configured to be coupled to one of the plurality of spring mechanisms. The attachment component has an attachment surface configured to be removably attached, during use, to the skin over the patella of the user such that the spring mechanism (to which the attachment component is attached) applies a tension force on the attachment component in an anterior direction.

In one example, the kit may include device 10 with a plurality of spring mechanisms 14 having different lengths, materials, thicknesses, and/or gauges, as described above. The kit may be employed by the user to apply different spring mechanisms depending on the amount of tension force required. By way of example, a lower tension spring mechanism 14 may be employed for minor patellofemoral conditions, while a spring mechanism 14 that supplies a higher tension force may be used to manage more extreme patellofemoral conditions. The kit advantageously allows a user to customize the level of treatment applied during use. The kit may also include a plurality of the connectors as shown in FIG. 7B or FIG. 8B.

EXAMPLES

The present invention may be further illustrated by reference to the following examples.

Example 1

Management of Patellofemoral Pain

The development of this device is the result of numerous attempts to alleviate the inventor's own patellofemoral pain due to early onset arthritis in the knees. Having previously used a variety of knee supports, braces, and taping methods along with physical therapy, the inventor had limited and varying reduction in knee discomfort after long sessions of running and cycling. After suffering years of knee discomfort, the inventor became acutely aware of where and when the pain presented itself.

It has been approximately 13 months since the user began using the device on his right knee (most problematic) while running and cycling. During that time the device has gone through several revisions and modifications to improve durability, but the function has been consistent, to pull the patella gently away from the femur in the trochlear groove.

Prior to using the device, the inventor relied on kinesiology taping or knee support/braces to help relieve knee discomfort. Throughout a 5 year period, long bike rides and runs of more than 1 hour were problematic, with knee discomfort increasing significantly whenever the inventor went beyond 1 hr.

Since the inventor began using the device, the inventor has logged over 100 hours of running (approx. 600 miles) and 150 hours of cycling (approx. 2250 miles). Running sessions typically ranged from ½ to 2 hours and cycling sessions ranged from 1 to 4 hours. The results of using the device were immediate as there was a significant reduction of discomfort on the inventor's very first ride and run. The reduction was particularly noticeable when the inventor cycled or ran beyond 1 hour, in which the inventor's knee felt great and the inventor was able to continue.

Example 2

X-Ray Evidence of Patella Realignment and Therapeutic Benefit

Figure 11:
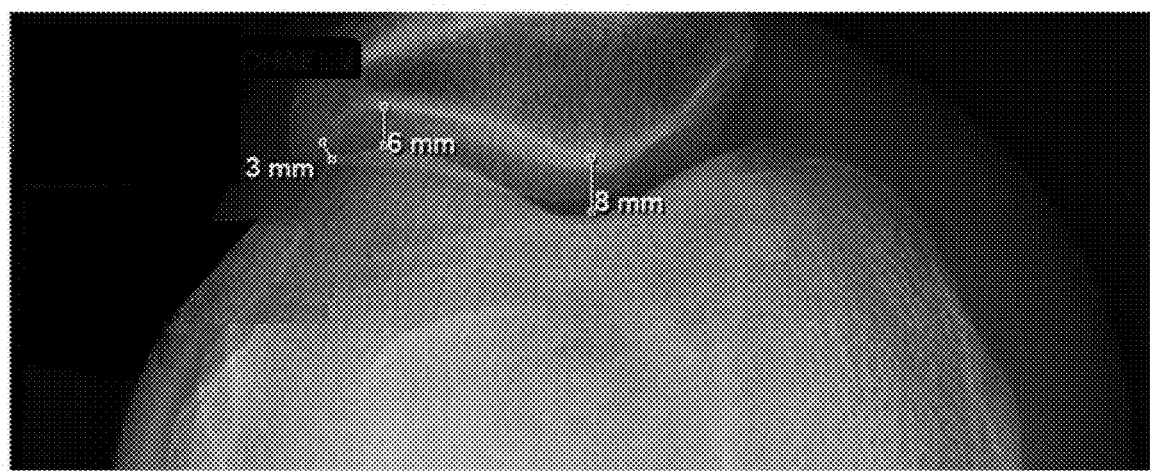
FIG. 11 is an x-ray of a user's knee without the device of the present invention prior to a period of frequent use.
Figure 12:
FIG. 12 is an x-ray of the user's knee without the device after approximately eight months of frequent use of the device.
Figure 13:
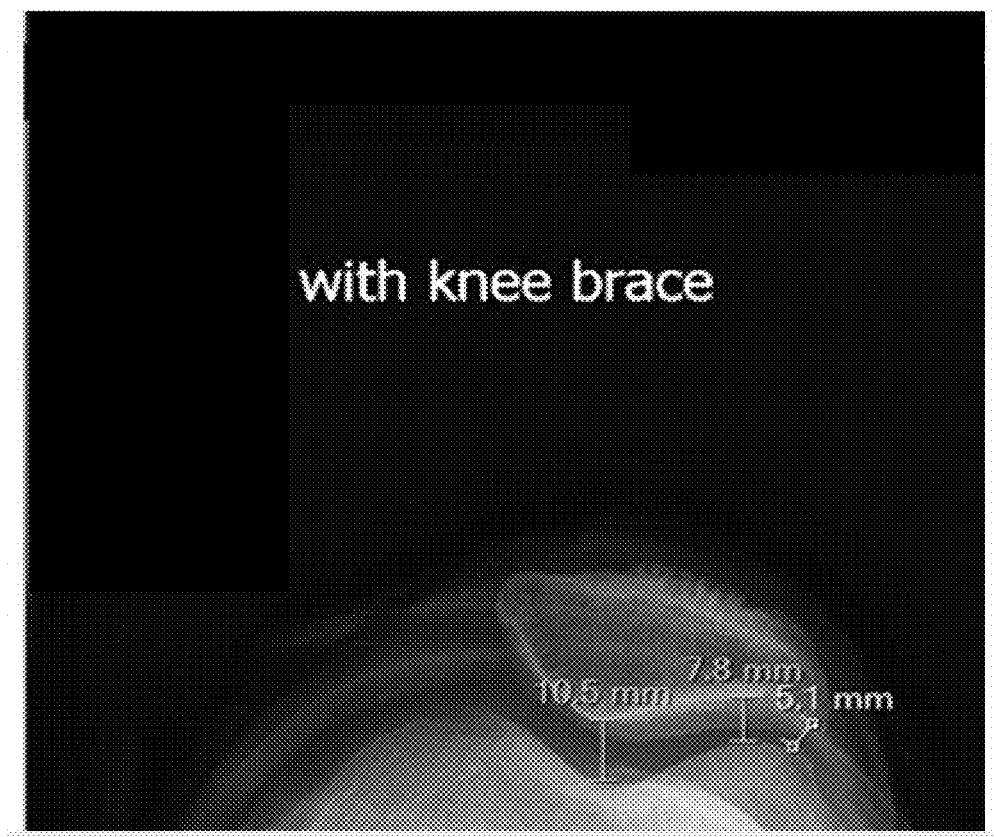
FIG. 13 is an x-ray of the user's knee with the device on after the approximately eight months of frequent use of the device.

An x-ray was performed on the user's knee without the device of the present invention as shown in FIG. 11. The x-ray showed a patellofemoral space of 8 mm (0.315 inches) and a lateral patellofemoral space of 3 mm (0.118 inches). After approximately eight months of daily use, x-rays were taken of the user's knee both with and without the device as shown in FIGS. 12 and 13, respectively. The x-rays in FIGS. 12 and 13 are of the same knee from the same perspective as FIG. 11. However, the image is flipped.

The x-rays without the device showed a 1 mm (0.039 inches) increase in the patellofemoral space resulting from the anterior lift on the patella during the daily use. A 1.2 mm (0.047 inches) increase (41%) in lateral patellofemoral space was also shown as a result of the daily use.

The x-rays taken with the device were compared to the x-rays taken without the device. The use of the device provided a further 1.5 mm (0.197 inches) increase in patellofemoral space and a further 0.9 mm (0.035 inches) increase in lateral patellofemoral space.

Example 3

Survey Data of Evidence of Performance

The device of the present invention was provided to six individuals suffering from chronic patella femoral pain syndrome. These individuals were instructions for wearing the device and also were provided with a self-administered WOMAC (Western Ontario and McMaster Universities) Osteoarthritis Index questionnaire that assessed four categories: (1) symptoms, (2) knee pain, (3) stiffness, and (4) physical function. These categories were further broken down into the following sub-categories:

Symptoms: (a) swelling, (b) grinding, clicking, or other noise, (c) catching or hanging up when moving, (d) straighten knee fully, and (e) bend knee fully Stiffness: (a) after first waking and (b) later in the day.

Pain: (a) during walking, (b) using stairs, (c) in bed, (d) sitting or lying, and (e) standing upright.

Physical Function: (a) descending stairs, (b) ascending stairs, (c) rising from sitting, (d) standing, (d) bending, (e) walking on a flat surface, (f) getting into/out of a car, (g) shopping, (h) putting on socks, (i) taking off socks, (j) rising from bed, (k) lying in bed, (m) getting in/out of bath, (n) sitting, (o) getting on/off toilet, (p) heavy domestic duties (moving boxes, scrubbing floors, etc.), and (s) light domestic duties (cooking, dusting, etc.).

Each of the symptoms categories was evaluated on a scale of 0-4 corresponding to: Never (0), Rarely (1), Sometimes (2), Often (3), and Always (4). Each of the other subcategories was scored on a scale of 0-4 corresponding to: None (0), Mild (1), Moderate (2), Severe (3), and Extreme (4). Higher scores indicate worse pain, stiffness, and functional limitations.

The survey was completed prior to use of the device of the present invention and after a month of daily use of the device of the invention. Results were averaged for the six users's and reported as a percentage of the maximum total score. The results reflect a significant reduction in the symptom score (from 31% to 6%), the stiffness score (from 41% to 13%), the pain score (from 40% to 7%), and the functional limitation score (from 36% to 6%). The total score was reduced from 32% to 5% following use of the device.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. For example, and without limitation, the general shape and appearance of the spring mechanism and anchor structures can be modified for purposes of manufacture and assembly without departing from the scope of the invention.

What is claimed is:

1. A device for managing patellofemoral pain comprising:
   a wearable anchor structure configured to be positioned adjacent to the knee joint of a user;
   a spring mechanism attachable, during use, to the wearable anchor structure at first and second attachment positions located laterally and medially of the knee joint, respectively; and
   an attachment component coupled to the spring mechanism, the attachment component having an attachment surface configured to be removably attached, during use, to the skin over the patella of the user,
   wherein the spring mechanism is sized and configured such that, during use, the spring mechanism is spaced apart from the user and the wearable anchor structure along its length between the first attachment position and the attachment component and between the attachment component and the second attachment position, whereby the spring mechanism applies a tension force on the attachment component in an anterior direction to anteriorly displace the patella of the user.

2. The device of claim 1 further comprising:
   a spacer element coupling the attachment component to the spring mechanism, wherein the spacer element is adjustable with respect to the spring mechanism to adjust a distance between the spring mechanism and the attachment component to adjust the tension force on the attachment component.

3. The device of claim 2, wherein the spacer element is a loop structure coupled to the spring mechanism.

4. The device of claim 3, wherein the coupling between the loop structure and the spring mechanism is adjustable to adjust an angle of the tension force on the attachment component.

5. The device of claim 2, wherein the spacer element is configured such that the distance between the spring mechanism and the attachment component is between about 0.125 inches to about 3 inches.

6. The device of claim 1, wherein the wearable anchor structure is a sleeve or wrap.

7. The device of claim 6, wherein the sleeve or wrap comprises a medial connector and a lateral connector.

8. The device according to claim 7, wherein the spring mechanism comprises first and second connectors that matingly engage with one or both of the medial and lateral connectors.

9. The device of claim 1, wherein the wearable anchor structure comprises a medial anchor member having an adhesive layer on one side of the medial anchor member and a medial connector on an opposing side of the medial anchor member, and a lateral anchor member having an adhesive layer on one side of the lateral anchor member and a lateral connector on an opposing side of the lateral anchor member.

10. The device according to claim 9, wherein the spring mechanism comprises first and second connectors that matingly engage with one or both of the medial and lateral connectors.

11. The device of claim 1, wherein the spring mechanism is a flexible strip.

12. The device according to claim 11, wherein the spring mechanism comprises one or more connectors at a first end of the flexible strip and one or more connectors at a second end of the flexible strip.

13. The device of claim 1 further comprising:
   a shield component configured to cover the attachment component in the anterior direction during use.

14. The device of claim 13, wherein the shield component is dome-shaped.

15. The device of claim 1, wherein the first and second attachment positions are adjustable to adjust the tension force on the attachment component.

16. The device of claim 1, where a length of the spring mechanism is adjustable to adjust the tension force on the attachment component.

17. The device of claim 1, wherein the attachment surface of the attachment component comprises an adhesive layer.

18. The device of claim 1, wherein the attachment component is fixedly attached to the spring mechanism.

19. A method of managing patellofemoral joint pain, the method comprising:
   providing a device comprising:
   a wearable anchor structure configured to be positioned adjacent to the knee joint of a user;
   a spring mechanism attachable, during use, to the wearable anchor structure at first and second attachment positions located laterally and medially of the knee joint, respectively; and
   an attachment component having an attachment surface configured to be removably attached, during use, to the skin over the patella of the user,
   wherein the spring mechanism is sized and configured such that, during use, the spring mechanism is spaced apart from the user and the wearable anchor structure along its length between the first attachment position and the attachment component and between the attachment component and the second attachment position, whereby the spring mechanism applies a tension force on the attachment component in an anterior direction to anteriorly displace the patella of the user;

positioning the wearable anchor structure adjacent to the knee joint of the user;

attaching the spring mechanism to the wearable anchor structure at the first and the second attachment positions located laterally and medially of the knee joint; and attaching the attachment surface of the attachment component to the skin over the patella of the user and coupling the attachment component to the spring mechanism to apply the tension force on the attachment component in the anterior direction from the spring mechanism.

20. The method of claim 19 further comprising:

adjusting the first and second attachment positions to adjust the tension force on the attachment component.

21. The method of claim 19 further comprising:

adjusting a length of the spring mechanism to adjust the tension force on the attachment component.

22. The method of claim 19 further comprising:

providing a spacer element coupling the attachment component to the spring mechanism; and adjusting the spacer element with respect to the spring mechanism to adjust a distance between the spring mechanism and the attachment component to adjust the tension force on the attachment component.

23. The method of claim 19 further comprising:

adjusting the positioning of the coupling between the spacer element and the spring mechanism to adjust an angle of the tension force on the attachment component.

24. A method of realigning a user's patella, the method comprising:

providing a prosthetic device comprising:

a wearable anchor structure configured to be positioned adjacent to the knee joint of a user having a misaligned patella;

a spring mechanism attachable, during use, to the wearable anchor structure at first and second attachment positions located laterally and medially of the knee joint, respectively; and an attachment component coupled to the spring mechanism, the attachment component having an attachment surface configured to be removably attached, during use, to the skin over the patella of the user, wherein the spring mechanism is sized and configured such that, during use, the spring mechanism is spaced apart from the user and the wearable anchor structure along its length between the first attachment position and the attachment component and between the attachment component and the second attachment position, whereby the spring mechanism applies a traction force on the attachment component in an anterior direction to anteriorly displace the patella of the user; and applying the prosthetic device about the knee of the user to apply the traction force anteriorly to displace the patella, whereby said applying is carried out repeatedly and periodically over a period of time to cause a realignment of the patella by increasing a space between the patella and the femur.

* * * * *